United States Patent
Kim et al.

(10) Patent No.: US 7,662,810 B2
(45) Date of Patent: Feb. 16, 2010

(54) 2-ARYLMETHYLAZETIDINE CARBAPENEM DERIVATIVES AND PREPARATION THEREOF

(75) Inventors: Bong-Jin Kim, Daejeon (KR); Jae-Hak Kim, Daejeon (KR); Jae-Yang Kong, Daejeon (KR); Heeyeong Cho, Daejeon (KR); Young-Ro Choi, Kunpo-si (KR); Chang-Seob Kim, Ansan-si (KR)

(73) Assignee: Korea Research Institute of Chemical Technology (KR)

( * ) Notice: Subject to any disclaimer, the term of this patent is extended or adjusted under 35 U.S.C. 154(b) by 511 days.

(21) Appl. No.: 11/578,007

(22) PCT Filed: Feb. 24, 2005

(86) PCT No.: PCT/KR2005/000509

§ 371 (c)(1),
(2), (4) Date: Oct. 6, 2006

(87) PCT Pub. No.: WO2006/025634

PCT Pub. Date: Mar. 9, 2006

(65) Prior Publication Data

US 2007/0244089 A1    Oct. 18, 2007

(30) Foreign Application Priority Data

Aug. 31, 2004    (KR) .................. 10-2004-0068821

(51) Int. Cl.
C07D 477/20    (2006.01)
A61K 31/407    (2006.01)
A61P 31/04    (2006.01)
C07D 205/04    (2006.01)
C07F 9/572    (2006.01)

(52) U.S. Cl. .................. 514/210.12; 540/350; 548/952

(58) Field of Classification Search ............ 514/210.12; 540/350

See application file for complete search history.

(56) References Cited

U.S. PATENT DOCUMENTS

| | | | | |
|---|---|---|---|---|
| 4,552,873 A | * | 11/1985 | Miyadera et al. | 514/210.12 |
| 5,534,510 A | * | 7/1996 | Abe et al. | 514/210.11 |
| 5,707,987 A | * | 1/1998 | Nakagawa et al. | 514/210.09 |
| 5,886,172 A | * | 3/1999 | Abe et al. | 540/350 |
| 6,051,569 A | * | 4/2000 | Ishiguro et al. | 514/210.12 |
| 7,001,897 B2 | * | 2/2006 | Kobayashi et al. | 514/210.12 |

FOREIGN PATENT DOCUMENTS

EP    472062 A1  *  2/1992

* cited by examiner

*Primary Examiner*—Mark L Berch
(74) *Attorney, Agent, or Firm*—Baker & Hostetler, LLP

(57) ABSTRACT

A 2-arylmethylazetidine carbapenem derivative of formula (I) or a pharmaceutically acceptable salt thereof exhibits a wide spectrum of antibacterial activities against Gram-positive and Gram-negative bacteria and excellent antibacterial activities against resistant bacteria such as methicillinresistant *Staphylococcus aureus* (MRSA) and quinolone-resistant strains (QRS):

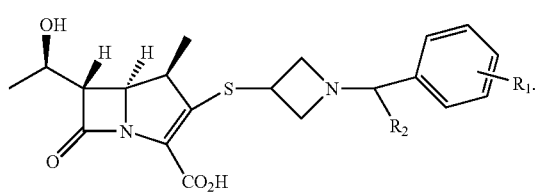

(I)

10 Claims, No Drawings

2-ARYLMETHYLAZETIDINE CARBAPENEM DERIVATIVES AND PREPARATION THEREOF

FIELD OF THE INVENTION

The present invention relates to 2-arylmethylazetidine carbapenem derivatives having a wide spectrum of antibacterial activities against Gram-positive and Gram-negative bacteria and excellent antibacterial activities against resistant bacteria such as methicillin-resistant *Staphylococcus aureus* (MRSA) and quinolone-resistant strains (QRS); a process for the preparation thereof; and an antibiotic composition comprising same.

BACKGROUND OF THE INVENTION

Since penicillin was firstly used clinically in 1940s, it had been known as a miracle medicine saving many lives against infectious diseases. However, it was not long till *Staphylococcus aureus* having resistance against penicillin appeared. In 1960s, methicillin, semi-synthetic penicillin, was developed and used to treat infectious diseases caused by penicillin-resistant *Staphylococcus aureus*, and in 1973, cefazolin was developed. But, methicillin-resistant *Staphylococcus aureus* (MRSA) and cefazolin-resistant strain appeared, and a number of antibiotics including cephalosporin, quinolone, carbapenem, monobactam and glycoside have been developed to deal with the resistant bacteria. However, penicillin-resistant *Streptococcus pneumococcus*, MRSA and other antibiotics-resistant bacteria continued to cast problems over the world.

Therefore, there has been a continual need to develop still new antibiotics having antibacterial activity against not only Gram-positive and Gram-negative bacteria but also resistant bacteria. Recently, it was reported that 2-arylcarbapenem compounds (L-695256 and L-742728, MERCK) showed good activity against MRSA, VRSA and VRE (Hugh rosen et al., *Sciences*, 703(1999)). WO 99/62906 reports that 2-benzothiazolethenyl carbapenem has good activity against MRSA. In addition, many antibiotics derived from carbapenem have been reported to show some activity against MRSA. For example, imipenem and meropenem are effective in treating infection by MRSA having weak resistance.

Accordingly, the present inventors have endeavored to develop an antibiotic having a wide spectrum of antibacterial activities against Gram-positive and Gram-negative bacteria, which can be used to treat infection by resistant bacteria such as MRSA.

SUMMARY OF THE INVENTION

Accordingly, it is an object of the present invention to provide a carbapenem derivative, which has excellent antibacterial activity and can be used to treat infection by resistant bacteria such as MRSA and QRS.

Another object of the present invention is to provide a process for the preparation of said carbapenem derivative.

A further object of the present invention is to provide an antibiotic composition comprising said carbapenem derivative as an active ingredient.

In accordance with one aspect of the present invention, there is provided a 2-arylmethylazetidine carbapenem derivative of formula (I) or a pharmaceutically acceptable salt thereof:

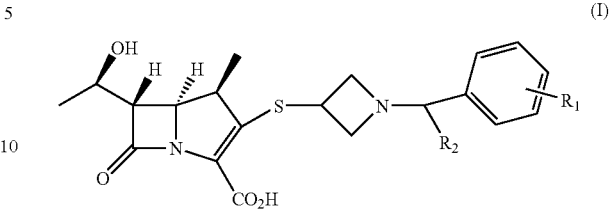

wherein,
$R_1$ is hydrogen, or one or more substituents selected from the group consisting of $C_{1-3}$ alkyl, $C_{1-3}$ alkyloxy, hydroxyl, amine, alkylamine, alkylthiol, trifluoromethyl and halogen; and
$R_2$ is hydrogen or $C_{1-3}$ alkyl.

In accordance with another aspect of the present invention, there is provided a process for the preparation of said carbapenem derivative, and an antibiotic composition comprising said carbapenem derivative or its pharmaceutically acceptable salt as an active ingredient.

DETAILED DESCRIPTION OF THE INVENTION

Examples of the desirable compounds of formula (I) according to the present invention are:

Potassium(1R,5S,6S)-2-(1-benzyl-azetidine-3-yl-thio)-6-[(1R)-1-hydroxyethyl]-1-methylcarbapen-2-em-3-carboxylate;

Potassium(1R,5S,6S)-2-[1-(4-methoxybenzyl)-azetidine-3-yl-thio]-6-[(1R)-1-hydroxyethyl]-1-methylcarbapen-2-em-3-carboxylate;

Potassium(1R,5S,6S)-2-[1-(3-methoxybenzyl)-azetidine-3-yl-thio]-6-[(1R)-1-hydroxyethyl]-1-methylcarbapen-2-em-3-carboxylate;

Potassium(1R,5S,6S)-2-[1-(2-methoxybenzyl)-azetidine-3-yl-thio]-6-[(1R)-1-hydroxyethyl]-1-methylcarbapen-2-em-3-carboxylate;

Potassium(1R,5S,6S)-2-[1-(3,4-dimethoxybenzyl)-azetidine-3-yl-thio]-6-[(1R)-1-hydroxyethyl]-1-methylcarbapen-2-em-3-carboxylate;

Potassium(1R,5S,6S)-2-[1-(4-chlorobenzyl)-azetidine-3-yl-thio]-6-[(1R)-1-hydroxyethyl]-1-methylcarbapen-2-em-3-carboxylate;

Potassium(1R,5S,6S)-2-[1-(4-fluorobenzyl)-azetidine-3-yl-thio]-6-[(1R)-1-hydroxyethyl]-1-methylcarbapen-2-em-3-carboxylate;

Potassium(1R,5S,6S)-2-[1-(3-trifluoromethylbenzyl)-azetidine-3-yl-thio]-6-[(1R)-1-hydroxyethyl]-1-methylcarbapen-2-em-3-carboxylate;

Potassium(1R,5S,6S)-2-{1-[(1R)-1-phenylethyl]-azetidine-3-yl-thio}-6-[(1R)-1-hydroxyethyl]-1-methylcarbapen-2-em-3-carboxylate;

Potassium(1R,5S,6S)-2-{1-[(1S)-1-phenylethyl]-azetidine-3-yl-thio}-6-[(1R)-1-hydroxyethyl]-1-methylcarbapen-2-em-3-carboxylate;

Potassium(1R,5S,6S)-2-[1-(4-methylbenzyl)-azetidine-3-yl-thio]-6-[(1R)-1-hydroxyethyl]-1-methylcarbapen-2-em-3-carboxylate; and Potassium(1R,5S,6S)-2-{1-[1-(4-bromophenyl)ethyl]-azetidine-3-yl-thio}-6-[(1R)-1-hydroxyethyl]-1-methylcarbapen-2-em-3-carboxylate.

The 2-arylmethylazetidine carbapenem derivative of the present invention may be prepared by a process comprising the steps of:

(a) subjecting compounds of formula (II) and formula (III) to a condensation reaction to obtain a carbapenem ester derivative of formula (IV); and (b) removing the carboxyl protecting group and the optional hydroxyl protecting group from the compound of formula (IV).

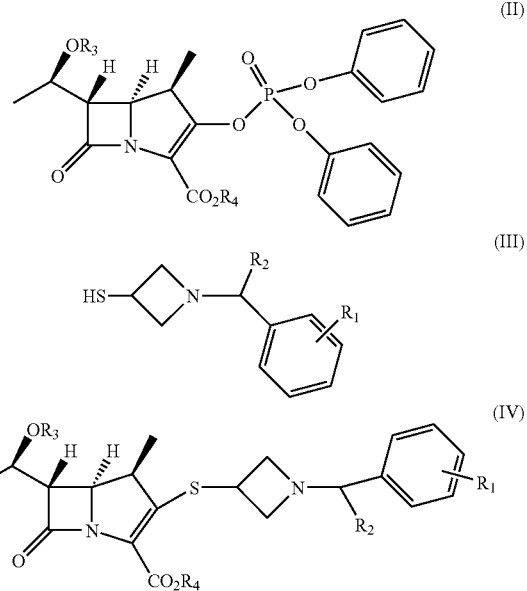

wherein, $R_1$ and $R_2$ have the same meanings as defined above;

$R_3$ is hydrogen or a hydroxyl protecting group; and $R_4$ is a carboxyl protecting group.

In the above process, the hydroxyl protecting groups may be one of the common hydroxyl protecting groups such as tert-butyldimethylsilyl and triethylsilyl groups, and the carboxyl protecting group may be one of the common carboxyl protecting groups such as p-nitrobenzyl, allyl and p-methoxybenzyl groups.

The condensation between p-nitrobenzyl-2-diphenylphosphoryl-6-tert-butyldimethylsilyloxyethyl-1-methyl-2-carbapenem-3-carboxylate of formula (II) ($R_3$=tert-butyldimethylsilyl, $R_4$=p-nitrobenzyl) and 1-allylmethyl-3-mercaptoazetidine derivative of formula (III) can be carried out in accordance with a conventional method.

For instance, the compound of formula (III) is dissolved in an anhydrous organic solvent, e.g., acetonitril, methylene chloride, tetrahydrofuran or acetone, preferably acetonitril, and cooled to a temperature ranging from −20° C. to 0° C. N,N-diisopropylethylamine or triethylamine is slowly added to the resulting solution, and the compound of formula (II) is added thereto. The above mixture is stirred at a temperature ranging from −20° C. to 0° C. for 2 to 4 hours, and the resulting product is separated in accordance with a conventional method to obtain the compound of formula (IV).

The hydroxyl protecting group ($R_3$) and the carboxyl protecting group ($R_4$) may be removed sequentially from the compound of formula (IV) in accordance with conventional methods, or, in case when the hydroxyl group is not protected, only the carboxyl protecting group is removed to obtain the compound of formula (I).

For instance, in case when a triethylsilyl hydroxyl protecting group ($R_3$) and a carboxyl protecting group ($R_4$) are to be removed sequentially, the compound of formula (IV) is dissolved in a mixture of tetrahydrofuran and water (4:1 (V:V)), an equivalent amount of 1 M aqueous trifluoroacetic acid solution is added thereto, and the resulting solution is stirred at room temperature for 30 to 60 min to remove the hydroxyl protecting group. Then, when $R_4$ is a p-nitrobenzyl group, it may be removed by catalytic hydrogenation, and when $R_4$ is an ally group, it may be removed by reacting the compound of formula (IV) with triphenylphosphine or tetrakis(triphenylphosphine)palladium under the presence of an organic acid or its salt (e.g., acetic acid, 2-ethylhexanonic acid and a sodium or potassium salt thereof).

The resulting compound may be purified by reverse-phase silica gel column chromatography, and lyophilized to obtain the compound of the formula (I) as an amorphous solid.

The compound of the formula (III) used in the present invention may be prepared according to Scheme (I).

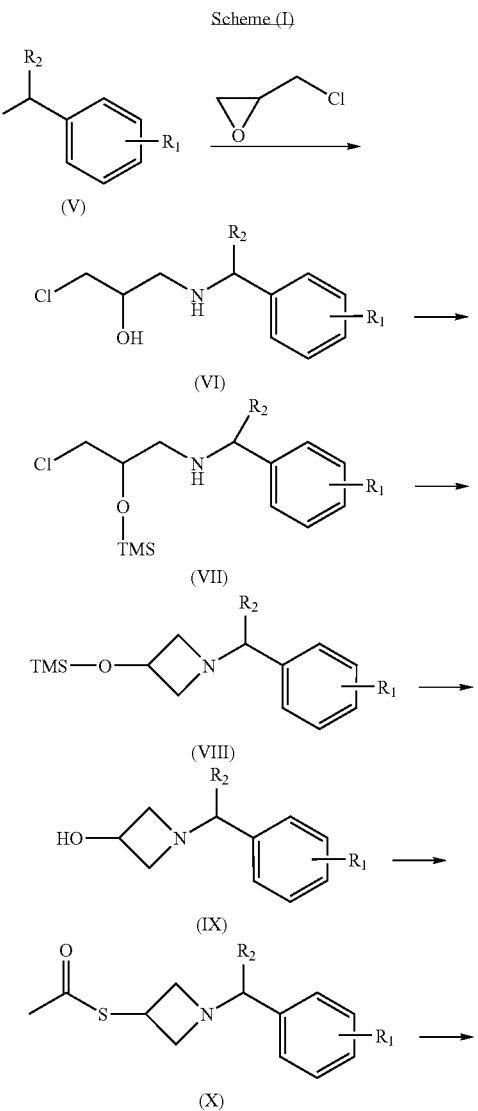

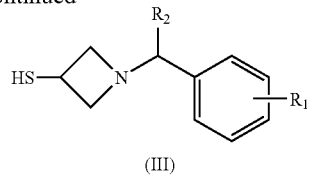

wherein, $R_1$ and $R_2$ have the same meanings as defined above.

Specifically, an aromatic amine (a compound of formula (V)) and epichlorohydrin are added to an organic solvent, the mixture is stirred for 24 to 48 hours to obtain a solid product, and the product is filtered to obtain a compound of formula (VI). The compound of formula (VI) and N-trimethylsilylacetamide are heated in an organic solvent for 3 to 5 hours, and the product is distilled under a reduced pressure to obtain a compound of formula (VII). Examples of the organic solvent used in the above reactions include ethyl ether, petroleum ether and ligroin, and petroleum ether is preferable.

The compound of formula (VII) is then dissolved in an organic solvent such as acetonitrile, tetrahydrofuran and methylene chloride, preferably in acetonitrile. An organic base such as triethylamine and diisopropylethylamine, preferably triethylamine, is added thereto, and the mixture is refluxed for 3 to 5 days to obtain a compound of formula (VIII). The compound of formula (VIII) is dissolved in an alcohol such as methanol and ethanol, preferably methanol, and an alkali such as sodium methoxide, lithium hydroxide and potassium tert-butoxide, preferably sodium methoxide, is added thereto. The mixture is stirred at room temperature for 30 min to 1 hour to obtain a compound of formula (IX), which is subsequently subjected to the Mitsunobu reaction to obtain a compound of formula (X). Specifically, diisopropylazodicarboxylate is added to a solution of triphenylphosphine in anhydrous tetrahydrofuran, and the mixture is reacted at 0° C. for 1 hour. Thioacetic acid and the compound of formula (IX) are added thereto, and the resulting mixture is reacted at room temperature for 2 to 4 hours to obtain a thioacetate derivative of formula (X).

The compound of formula (X) is then hydrolyzed by treating with a conventional base (e.g., 2 N potassium hydroxide or sodium hydroxide) in an alcohol to obtain a thiol compound of formula (III), which is used for the preparation of the compound of formula (IV) without further purification.

The inventive compounds of formula (I) exhibit a wide spectrum of antibacterial activities against Gram-positive and Gram-negative bacteria, and excellent antibacterial activity against penicillin-resistant *Streptococcus pneumococcus*, MRSA, QRSA and vancomycin-Resistant *Enterococci* (VRE).

Therefore, the present invention provides an antibacterial composition comprising a carbapenem derivative of formula (I) or its pharmaceutically acceptable salt as an active ingredient in combination with a pharmaceutically acceptable carrier.

The pharmaceutical composition of the present invention may include the active ingredient in an amount of 0.1 to 75% by weight, preferably 1 to 50% by weight, based on the total weight of the composition.

The pharmaceutical composition of the present invention may be administered orally or parenterally. An oral formulation may be in the form of a tablet, pill, soft or hard gelatin capsule, solution, suspension, emulsion, syrup, powder and the like, and the formulation may include diluents (e.g., lactose, dextrose, sucrose, mannitol, sorbitol, cellulose and glycine), lubricants (e.g., silica, talc, stearic acid, a magnesium or calcium salt thereof and polyethylene glycol). The tablet may include binders such as magnesium aluminum silicate, starch paste, gelatin, tragacanth, methylcellulose, sodium carboxymethylcellulose and polyvinylpyrrolidin. The formulation may additionally include disintegrants such as starch, agar, and alginic acid or its sodium salt, mixture and/or absorbents, colorants, flavoring agents and sweeteners.

Also, a representative parenteral formulation is an injection formulation, preferably an isotonic solution or suspension.

The pharmaceutical composition may be sterilized and/or include additives such as preservatives, stabilizers, wetting agents, emulsifiers, salts or buffers for osmotic control and any other therapeutically useful materials. The composition may be formulated by employing a conventional method such as mixing, granulating and coating methods.

A typical daily dose of the compound of formula (I) or a pharmaceutically acceptable salt thereof may range from 2.5 to 100 mg/kg body weight, preferably 5 to 60 mg/kg body weight in case of mammals including human, and can be administered in a single dose or in divided doses orally or parenterally.

The following examples are intended to further illustrate the present invention without limiting its scope.

Preparation Examples 1 to 12

Preparation of 1-substituted benzylamino-3-chloropropane-2-ol

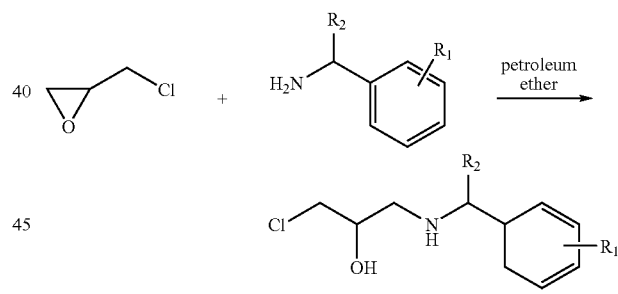

Preparation Example 1

1-benzylamino-3-chloropropane-2-ol

Epichlorohydrin (39 ml, 0.5 mol) and benzylamine (54.6 ml, 0.5 mol) were dissolved in petroleum ether (500 ml), stirred at room temperature for 48 hours, and filtered. The resulting solid product was dissolved in toluene (50 ml), and normal hexane (500 ml) was added to the resulting solution to obtain the title compound as a crystalline form in a yield of 43%.

$^1$H NMR (200 MHz, CDCl$_3$): δ 2.76 (m, 2H), 3.55 (d, J=5.3 Hz, 2H), 3.81 (s, 2H), 3.86 (m, 1H), 7.32 (m, 5H).

The procedure of Preparation Example 1 was repeated employing appropriate starting materials to obtain the compounds of Preparation Examples 2 to 12, respectively.

Preparation Example 2

1-chloro-3-(4-methoxybenzylamino)propane-2-ol

Yield: 53.4%;
$^1$H NMR (200 MHz, CDCl$_3$): δ 2.79 (m, 2H), 3.55 (d, J=5.4 Hz, 2H), 3.76 (s, 2H), 3.80 (s, 3H), 3.91 (m, 1H), 6.86 (d, J=8.4 Hz, 2H), 7.24 (d, J=8.4 Hz, 2H).

Preparation Example 3

1-chloro-3-(3-methoxybenzylamino)propane-2-ol

Yield: 48.7%;
$^1$H NMR (200 MHz, CDCl$_3$): δ 2.78 (m, 2H), 3.56 (d, J=5.5 Hz, 2H), 3.79 (s, 2H), 3.81 (s, 3H), 3.86 (m, 1H), 6.82 (m, 3H), 7.21 (m, 1H).

Preparation Example 4

1-chloro-3-(2-methoxybenzylamino)propane-2-ol

Yield: 50.8%;
$^1$H NMR (200 MHz, CDCl$_3$): δ 2.71 (m, 2H), 3.51 (d, J=5.9 Hz, 2H), 3.79 (s, 2H), 3.84 (s, 3H), 3.86 (m, 1H), 6.90 (m, 2H), 7.21 (m, 2H).

Preparation Example 5

1-chloro-3-(3,4-dimethoxybenzylamino)propane-2-ol

Yield: 38.6%;
$^1$H NMR (200 MHz, CDCl$_3$): δ 2.71 (m, 2H), 3.49 (d, J=5.5 Hz, 2H), 3.92 (m, 9H), 6.80 (m, 3H).

Preparation Example 6

1-chloro-3-(4-chlorobenzylamino)propane-2-ol

Yield: 45.3%;
$^{1H}$NMR (200 MHz, CDCl$_3$): δ 2.78 (m, 2H), 3.58 (d, J=5.3 Hz, 2H), 3.78 (s, 2H), 3.88 (m, 1H), 7.28 (m, 4H).

Preparation Example 7

1-chloro-3-(4-fluorobenzylamino)propane-2-ol

Yield: 34.4%;
$^1$H NMR (200 MHz, CDCl$_3$): δ 2.78 (m, 2H), 3.57 (d, J=5.3 Hz, 2H), 3.79 (s, 2H), 3.90 (m, 1H), 7.01 (m, 2H), 7.29 (m, 2H).

Preparation Example 8

1-chloro-3-(3-trifluoromethylbenzylamino)propane-2-ol

Yield: 50.8%;
$^1$H NMR (200 MHz, CDCl$_3$): δ 2.79 (m, 2H), 3.60 (d, J=5.3 Hz, 2H), 3.87 (m, 3H), 7.50 (m, 4H).

Preparation Example 9

1-chloro-3-[(1R)-1-phenylethylamino]propane-2-ol

Yield: 76.2%;
$^1$H NMR (200 MHz, CDCl$_3$): δ 1.39 (d, J=6.5 Hz, 3H), 2.60 (m, 2H), 3.51 (m, 2H), 3.79 (m, 2H), 7.31 (m, 5H).

Preparation Example 10

1-chloro-3-[(1S)-1-phenylethylamino]propane-2-ol

Yield: 76.2%;
$^1$H NMR (200 MHz, CDCl$_3$): δ 1.39 (d, J=6.5 Hz, 3H), 2.61 (m, 2H), 3.51 (m, 2H), 3.80 (m, 2H), 7.32 (m, 5H).

Preparation Example 11

1-chloro-3-(4-methylbenzylamino)propane-2-ol

Yield: 48%;
$^1$H NMR (300 MHz, CDCl$_3$): δ 2.24 (bs, 2H), 2.34 (s, 3H), 2.67~2.86 (m, 2H), 3.55 (d, J=5.4 Hz, 2H), 3.77 (d, J=1.8 Hz, 2H), 3.88 (m, 1H), 7.13 (d, J=8.1 Hz, 2H), 7.18 (d, J=8.1 Hz, 2H).

Preparation Example 12

1-chloro-3-[1-(4-bromophenyl)ethylamino]propane-2-ol

Yield: 75%;
$^1$H NMR (300 MHz, CDCl$_3$): δ 1.34 (d, J=6.6 Hz, 3H) 2.58 (m, 2H), 3.52 (m, 2H), 3.73 (m, J=5.1 Hz, 1H), 4.12 (dd, 1H) 7.15 (m, 2H), 7.41 (m, 2H).

Preparation Examples 13 to 24

Preparation of (3-chloro-2-trimethylsilyloxypropyl)-substituted arlylamine

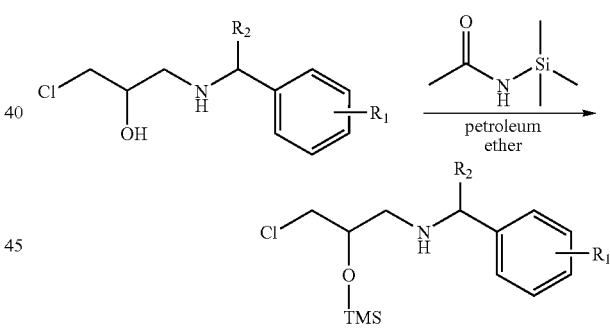

Preparation Example 13

1-benzyl-(3-chloro-2-trimethylsilyl-propyl)-amine

1-Benzylamino-3-chloropropane-2-ol (42.2 g, 0.21 mol) prepared in Preparation Example 1 was dissolved in petroleum ether (700 ml). N-(trimethylsilyl)acetamide (30.5 g, 0.23 mol) was added thereto, and refluxed with stirring for 3 hours. After removing solid precipitates by filtration, the filtrate was concentrated under a reduced pressure to obtain 54 g (yield: 95%) of the title compound.
$^1$H NMR (200 MHz, CDCl$_3$): δ 0.51 (s, 9H), 3.08 (m, 2H), 3.78 (s, 2H), 3.80 (m, 2H), 7.33 (m, 5H).

The procedure of Preparation Example 13 was repeated employing each of the compounds of Preparation Example 2 to 12 as a starting material to obtain the compounds of Preparation Examples 14 to 24, respectively.

Preparation Example 14

(3-chloro-2-trimethylsilyloxypropyl)-(4-methoxybenzyl)amine

Yield: 97%;
$^1$H NMR (200 MHz, CDCl$_3$): δ 0.15 (s, 9H), 2.71 (m, 2H), 3.56 (m, 2H), 3.74 (s, 2H), 3.80 (s, 3H), 3.96 (m, 1H), 6.85 (d, J=8.6 Hz, 2H), 7.23 (d, J=8.4 Hz, 2H).

Preparation Example 15

(3-chloro-2-trimethylsilyloxypropyl)-(3-methoxybenzyl)amine

Yield: 97.3%;
$^1$H NMR (200 MHz, CDCl$_3$): δ 0.15 (s, 9H), 2.75 (m, 2H), 3.52 (m, 2H), 3.77 (s, 2H), 3.81 (s, 3H), 3.95 (m, 1H), 6.80 (m, 1H), 6.88 (m, 2H), 7.26 (m, 1H).

Preparation Example 16

(3-chloro-2-trimethylsilyloxypropyl)-(2-methoxybenzyl)amine

Yield: 86.7%;
$^1$H NMR (200 MHz, CDCl$_3$): δ 0.14 (s, 9H), 2.69 (m, 2H), 3.52 (m, 2H), 3.79 (s, 2H), 3.83 (s, 3H), 3.98 (m, 1H), 6.89 (m, 2H), 7.21 (m, 2H).

Preparation Example 17

(3-chloro-2-trimethylsilyloxypropyl)-(3,4-dimethoxybenzyl)amine

Yield: 93.2%;
$^1$H NMR (200 MHz, CDCl$_3$): δ 0.15 (s, 9H), 2.71 (m, 2H), 3.55 (m, 2H), 3.75 (s, 2H), 3.87 (s, 3H), 3.88 (s, 3H), 3.97 (m, 1H), 6.83 (s, 2H), 6.89 (s, 1H).

Preparation Example 18

(3-chloro-2-trimethylsilyloxypropyl)-(4-chlorobenzyl)amine

Yield: 90.7%;
$^1$H NMR (200 MHz, CDCl$_3$): δ 0.14 (s, 9H), 2.72 (m, 2H), 3.56 (m, 2H), 3.77 (s, 2H), 3.94 (m, 3H), 7.27 (m, 4H).

Preparation Example 19

(3-chloro-2-trimethylsilyloxypropyl)-(4-fluorobenzyl)amine

Yield: 90.7%;
$^1$H NMR (200 MHz, CDCl$_3$): δ 0.14 (s, 9H), 2.71 (m, 2H), 3.53 (m, 2H), 3.76 (s, 2H), 3.95 (m, 1H), 7.04 (m, 2H), 7.28 (m, 2H).

Preparation Example 20

(3-chloro-2-trimethylsilyloxypropyl)-(3-trifluoromethylbenzyl)amine

Yield: 98%;
$^1$H NMR (200 MHz, CDCl$_3$): δ 0.15 (s, 9H), 2.78 (m, 2H), 3.58 (m, 2H), 3.87 (s, 2H), 3.95 (m, 1H), 7.50 (m, 3H), 7.60 (s, 1H).

Preparation Example 21

(3-chloro-2-trimethylsilyloxypropyl)-[(1R)-1-phenylethyl]amine

Yield: 97%;
$^1$H NMR (200 MHz, CDCl$_3$): δ 0.14 (s, 9H), 1.35 (d, J=6.5 Hz, 3H), 2.58 (m, 2H), 3.52 (m, 2H), 3.75 (m, 1H), 3.91 (m, 1H), 7.29 (m, 5H).

Preparation Example 22

(3-chloro-2-trimethylsilyloxypropyl)-[(1S)-1-phenylethyl]amine

Yield: 97%;
$^1$H NMR (200 MHz, CDCl$_3$): δ 0.14 (s, 9H), 1.35 (d, J=6.5 Hz, 3H), 2.58 (m, 2H), 3.55 (m, 2H), 3.71 (m, 1H), 3.88 (m, 1H), 7.30 (m, 5H).

Preparation Example 23

(3-chloro-2-trimethylsilyloxypropyl)-(4-methylbenzyl)amine

Yield: 94%;
$^1$H NMR (300 MHz, CDCl$_3$): δ 0.14 (s, 9H), 2.32 (s, 3H), 2.65~2.79 (m, 2H), 3.44~3.59 (m, 2H), 3.74 (s, 2H), 3.94 (m, 1H), 7.10 (d, J=7.8 Hz, 2H), 7.18 (d, J=7.8 Hz, 2H).

Preparation Example 24

(3-chloro-2-trimethylsilyloxypropyl)-[1-(4-bromophenyl)ethyl]amine

Yield: 95% (step 2);
$^1$H NMR (300 MHz, CDCl$_3$): δ 0.15 (s, 9H), 1.31 (d, J=6.6 Hz, 3H), 2.45~2.67 (m, 2H), 3.39~3.52 (m, 2H), 3.70 (m, J=5.1 Hz, 1H), 3.88 (m, 1H), 7.19 (d, J=6.3 Hz, 2H), 7.42 (d, J=6.9 Hz, 2H).

Preparation Examples 25 to 36

Preparation of 1-substituted benzyl-3-trimethylsilyloxy-azetidine

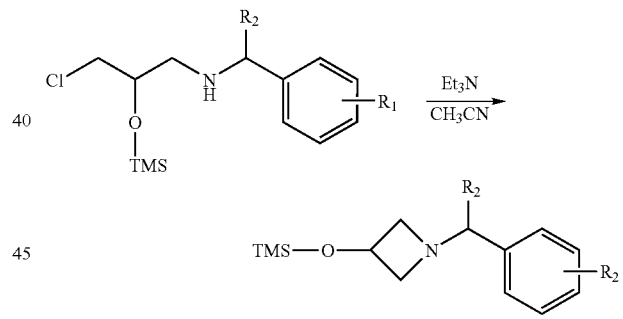

Preparation Example 25

1-benzyl-3-trimethylsilyloxy-azetidine

1-Benzyl-(3-chloro-2-trimethylsilyloxy-propyl)amine (2.15 g, 7.91 mmol) prepared in Preparation Example 13 was dissolved in acetonitrile (10 ml), triethylamine (1.54 g, 11.07 mmol) was added thereto, refluxed with stirring for 3 days, and cooled to room temperature. After removing solid precipitates by filtration, the filtrate was concentrated under a reduced pressure to obtain 1.8 g (yield: 96%) of the title compound.

$^1$H NMR (200 MHz, CDCl$_3$): δ 0.09 (s, 9H), 3.08 (m, 2H), 3.78 (s, 2H), 3.80 (m, 2H), 4.50 (m, 1H), 7.33 (m, 5H).

The procedure of Preparation Example 25 was repeated employing each of the compounds of Preparation Examples 14 to 24 as a starting material to obtain the compounds of Preparation Examples 26 to 36, respectively.

Preparation Example 26

1-(4-methoxybenzyl)-3-trimethylsilyloxy-azetidine

Yield: 98.4%;
$^1$H NMR (200 MHz, CDCl$_3$): δ 0.08 (s, 9H), 2.86 (m, 2H), 3.56 (s, 2H), 3.61 (m, 2H), 3.78 (s, 3H), 4.41 (m, 1H), 6.84 (d, J=8.8 Hz, 2H) 7.17 (d, J=8.8 Hz, 2H).

Preparation Example 27

1-(3-methoxybenzyl)-3-trimethylsilyloxy-azetidine

Yield: 88%;
$^1$H NMR (200 MHz, CDCl$_3$): δ 0.08 (s, 9H), 2.98 (m, 2H), 3.61 (s, 2H), 3.65 (m, 2H), 3.80 (s, 3H), 4.41 (m, 1H), 6.82 (m, 3H), 7.23 (m, 1H).

Preparation Example 28

1-(2-methoxybenzyl)-3-trimethylsilyloxy-azetidine

Yield: 89%;
$^1$H NMR (200 MHz, CDCl$_3$): δ 0.09 (s, 9H), 2.93 (m, 2H), 3.62 (s, 3H), 3.81 (m, 4H), 3.78 (s, 3H), 4.41 (m, 1H), 6.83 (m, 2H), 7.21 (d, J=7.3 Hz, 2H).

Preparation Example 29

1-(3,4-dimethoxybenzyl)-3-trimethylsilyloxy-azetidine

Yield: 85.1%;
$^1$H NMR (200 MHz, CDCl$_3$): δ 0.09 (s, 9H), 2.88 (m, 2H), 3.58 (s, 2H), 3.60 (m, 2H), 3.86 (s, 3H), 3.87 (s, 3H), 4.20 (m, 1H), 6.79 (s, 2H), 6.82 (s, 1H).

Preparation Example 30

1-(4-chlorobenzyl)-3-trimethylsilyloxy-azetidine

Yield: 95%;
$^1$H NMR (200 MHz, CDCl$_3$): δ 0.08 (s, 9H), 2.82 (m, 2H), 3.57 (s, 2H), 3.80 (m, 2H), 4.40 (m, 1H), 7.21 (m, 4H).

Preparation Example 31

1-(4-fluorobenzyl)-3-trimethylsilyloxy-azetidine

Yield: 90%;
$^1$H NMR (200 MHz, CDCl$_3$): δ 0.08 (s, 9H), 2.82 (m, 2H), 3.56 (s, 2H), 3.59 (m, 2H), 4.40 (m, 1H), 6.97 (m, 2H), 7.23 (m, 2H).

Preparation Example 32

1-(3-trifluoromethylbenzyl)-3-trimethylsilyloxy-azetidine

Yield: 91%;
$^1$H NMR (200 MHz, CDCl$_3$): δ 0.09 (s, 9H), 2.90 (m, 2H), 3.61 (m, 4H), 4.42 (m, 1H), 7.43 (m, 4H).

Preparation Example 33

1-[(1R)-1-phenylethyl]-3-trimethylsilyloxy-azetidine

Yield: 31%;
$^1$H NMR (200 MHz, CDCl$_3$): δ 0.08 (s, 9H), 1.24 (d, J=6.5 Hz, 3H), 2.70 (t, J=6.9 Hz, 1H), 2.88 (t, J=6.9 Hz, 1H), 3.29 (m, 2H), 3.78 (m, 1H), 4.39 (m, 1H), 7.31 (m, 5H).

Preparation Example 34

1-[(1S)-1-phenylethyl]-3-trimethylsilyloxy-azetidine

Yield: 41%;
$^1$H NMR (200 MHz, CDCl$_3$): δ 0.08 (s, 9H), 1.24 (d, J=6.5 Hz, 3H), 2.70 (t, J=6.9 Hz, 1H), 2.88 (t, J=6.9 Hz, 1H), 3.31 (m, 2H), 3.78 (m, 1H), 4.38 (m, 1H), 7.28 (m, 5H).

Preparation Example 35

1-(4-methylbenzyl)-3-trimethylsilyloxy-azetidine

Yield: 75%;
$^1$H NMR (300 MHz, CDCl$_3$): δ 0.10 (s, 9H), 2.32 (s, 3H), 2.94 (m, 2H), 3.62 (s, 2H), 3.69 (m, 2H), 4.43 (m, 1H), 7.10 (d, 2H), 7.18 (d, 2H).

Preparation Example 36

1-[-(4-bromophenyl)ethyl]-3-trimethylsilyloxy-azetidine

Yield: 78%;
$^1$H NMR (300 MHz, CDCl$_3$): δ 0.10 (s, 9H), 1.19 (d, J=6.6 Hz, 3H), 2.77 (m, 1H), 2.86 (m, 1H), 3.25 (dd, J=6.6 Hz, J=12.9 Hz, 1H), 3.41 (m, 1H), 3.66 (m, 1H), 4.41 (m, J=5.7 Hz, 1H), 7.18 (d, J=13.2 Hz, 2H), 7.44 (d, J=13.2 Hz, 2H).

Preparation Examples 37 to 48

Preparation of 1-substituted benzyl-azetidine-3-ol

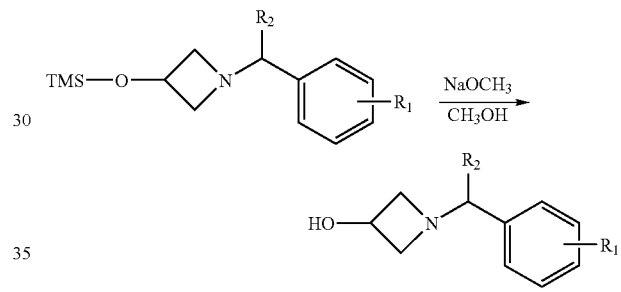

Preparation Example 37

1-benzyl-azetidine-3-ol

1-Benzyl-3-trimethylsilyloxy-azetidine (1.8 g, 7.65 mmol) prepared in preparation example 25 was dissolved in methanol (9 ml), sodium methoxide (826 mg, 15.29 mmol) was added thereto, and stirred at room temperature for 30 min. The solvent was removed by evaporation under a reduced pressure, and the residue was extracted using ethyl acetate. The organic extract layer was washed with water, dried over anhydrous magnesium sulfate, and concentrated under a reduced pressure, to obtain 0.964 g (yield: 77%) of the title compound.

$^1$H NMR (200 MHz, CDCl$_3$): δ 2.95 (m, 2H), 3.61 (m, 4H), 4.42 (m, 1H), 7.27 (m, 5H).

The procedure of Preparation Example 37 was repeated employing each of the compounds of Preparation Examples 26 to 36 as a starting material to obtain the compounds of Preparation Examples 38 to 48, respectively.

Preparation Example 38

1-(4-methoxybenzyl)-azetidine-3-ol

Yield: 100%;
$^1$H NMR (200 MHz, CDCl$_3$): δ 2.91 (m, 2H), 3.53 (s, 2H), 3.57 (m, 2H), 3.78 (s, 3H), 4.41 (m, 1H), 6.83 (d, J=9.0 Hz, 2H), 7.15 (d, J=8.4 Hz, 2H).

Preparation Example 39

1-(3-methoxybenzyl)-azetidine-3-ol

Yield: 42%;
$^1$H NMR (200 MHz, CDCl$_3$): δ 2.99 (m, 2H), 3.60 (s, 2H), 3.63 (m, 2H), 3.80 (s, 3H), 4.41 (m, 1H), 6.83 (m, 3H), 7.21 (m, 1H).

Preparation Example 40

1-(2-methoxybenzyl)-azetidine-3-ol

Yield: 53%;
$^1$H NMR (200 MHz, CDCl$_3$): δ 2.99 (m, 2H), 3.63 (s, 2H), 3.63 (m, 2H), 3.80 (s, 3H), 4.39 (m, 1H), 6.87 (m, 2H), 7.26 (d, J=7.3 Hz, 2H).

Preparation Example 41

1-(3,4-dimethoxybenzyl)-azetidine-3-ol

Yield: 40%;
$^1$H NMR (200 MHz, CDCl$_3$): δ 2.91 (m, 2H), 3.54 (s, 2H), 3.58 (m, 2H), 3.85 (s, 3H), 3.86 (s, 3H), 4.41 (m, 1H), 6.78 (s, 2H), 6.81 (s, 1H).

Preparation Example 42

1-(4-chlorobenzyl)-azetidine-3-ol

Yield: 66%;
$^1$H NMR (200 MHz, CDCl$_3$): δ 2.91 (m, 2H), 3.57 (s, 2H), 3.60 (m, 2H), 4.41 (m, 1H), 7.22 (m, 2H).

Preparation Example 43

1-(4-fluorobenzyl)-azetidine-3-ol

Yield: 61%;
$^1$H NMR (200 MHz, CDCl$_3$): δ 2.91 (m, 2H), 3.57 (s, 2H), 3.58 (m, 2H), 4.43 (m, 1H), 7.03 (m, 2H), 7.23 (m, 2H).

Preparation Example 44

1-(3-trifluoromethylbenzyl)-azetidine-3-ol

Yield: 64%;
$^1$H NMR (200 MHz, CDCl$_3$): δ 2.98 (m, 2H), 3.69 (m, 4H), 4.49 (m, 1H), 7.44 (m, 4H).

Preparation Example 45

1-[(1R)-1-phenylethyl]-azetidine-3-ol

Yield: 59%;
$^1$H NMR (200 MHz, CDCl$_3$): 1.25 (d, J=6.5 Hz, 3H), 2.90 (m, 2H), 3.38 (m, 2H), 3.70 (m, 1H), 4.40 (m, 1H), 4.78 (bs, 1H), 7.27 (m, 5H).

Preparation Example 46

1-[(1S)-1-phenylethyl]-azetidine-3-ol

Yield: 63%;
$^1$H NMR (200 MHz, CDCl$_3$): 1.25 (d, J=6.5 Hz, 3H), 2.90 (m, 2H), 3.38 (m, 2H), 3.71 (m, 1H), 4.40 (m, 1H), 4.50 (bs, 1H), 7.27 (m, 5H).

Preparation Example 47

1-(4-methylbenzyl)-azetidine-3-ol

Yield: 65%;
$^1$H NMR (300 MHz, CDCl$_3$): δ 2.32 (s, 3H), 2.92 (m, 2H), 3.53 (m, 4H), 4.38 (m, 1H), 7.09 (s, 4H).

Preparation Example 48

1-[1-(4-bromophenyl)ethyl]-azetidine-3-ol

Yield: 61%;
$^1$H NMR (300 MHz, CDCl$_3$): δ 1.19 (d, J=6.6 Hz, 3H), 2.76 (m, 1H), 2.88 (m, 1H), 3.24 (dd, J=6.6 Hz, J=12.9 Hz, 1H), 3.37 (m, 1H), 3.69 (m, 1H), 4.40 (m, J=5.7 Hz, 1H), 7.15 (d, J=13.2 Hz, 2H), 7.41 (d, J=13.2 Hz, 2H).

Preparation Examples 49 to 60

Preparation of 1-substituted benzyl-3-acetylthio-azetidine

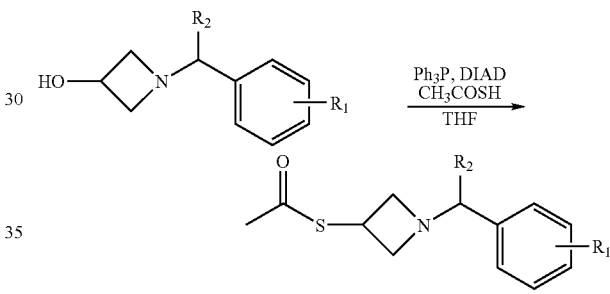

Preparation Example 49

1-benzyl-3-acetylthio-azetidine

Triphenylphosphine (3.08 g, 11.76 mmol) was dissolved in anhydrous tetrahydrofuran (THF) (30 ml). Oxygen was completely removed by passing nitrogen through the mixture, and the mixture was cooled to 0° C. Diisopropylazodicarboxylate (2.3 ml, 11.76 mmol) was added thereto, and stirred at 0° C. for 1 hour. Added slowly to the mixture in succession were thioacetic acid (840 μl, 11.76 mmol) and 1-benzyl-azetidine-3-ol (960 mg, 5.88 mmol) prepared in Preparation Example 37 and dissolved in tetrahydrofuran (20 ml). The resulting solution was heated to room temperature, stirred for 2 hours and concentrated under a reduced pressure to remove the solvent. The concentrate was dissolved in ethyl acetate, washed with water, dried over anhydrous magnesium sulfate and concentrated under a reduced pressure. The resulting residue was purified by column chromatography (eluent–ethyl acetate/normal hexane=1/1) to obtain 1.1 g (yield: 83%) of the title compound.

$^1$H NMR (200 MHz, CDCl$_3$): 2.31 (s, 3H), 3.10 (m, 2H), 3.61 (s, 2H), 3.70 (m, 2H), 4.15 (m, 1H), 7.26 (m, 5H).

The procedure of Preparation Example 49 was repeated employing each of the compounds of Preparation Examples 38 to 48 as a starting material to obtain the compounds of Preparation Examples 50 to 60, respectively.

Preparation Example 50

1-(4-methoxybenzyl)-3-acetylthio-azetidine

Yield: 83%;
$^1$H NMR (200 MHz, CDCl$_3$): 2.27 (s, 3H), 3.05 (m, 2H), 3.53 (s, 2H), 3.66 (m, 2H), 3.77 (s, 3H), 4.12 (m, 1H), 6.81 (d, J=8.8 Hz, 2H), 7.17 (d, J=8.8 Hz, 2H).

Preparation Example 51

1-(3-methoxybenzyl)-3-acetylthio-azetidine

Yield: 100%;
$^1$H NMR (200 MHz, CDCl$_3$): 2.29 (s, 3H), 3.08 (m, 2H), 3.59 (s, 2H), 3.71 (m, 2H), 3.80 (s, 3H), 4.15 (m, 1H), 6.81 (m, 3H), 7.21 (m, 1H).

Preparation Example 52

1-(2-methoxybenzyl)-3-acetylthio-azetidine

Yield: 33%;
$^1$H NMR (200 MHz, CDCl$_3$): 2.29 (s, 3H), 3.12 (m, 2H), 3.64 (s, 2H), 3.76 (m, 2H), 3.81 (s, 3H), 4.18 (m, 1H), 6.89 (m, 2H), 7.26 (d, J=7.5 Hz, 2H).

Preparation Example 53

1-(3,4-dimethoxybenzyl)-3-acetylthio-azetidine

Yield: 59%;
$^1$H NMR (200 MHz, CDCl$_3$): 2.29 (s, 3H), 3.07 (m, 2H), 3.55 (s, 2H), 3.69 (m, 2H), 3.85 (s, 3H), 3.88 (s, 3H), 4.18 (m, 1H), 6.78 (s, 2H), 6.81 (s, 1H).

Preparation Example 54

1-(4-chlorobenzyl)-3-acetylthio-azetidine

Yield: 88%;
$^1$H NMR (200 MHz, CDCl$_3$): 2.29 (s, 3H), 3.08 (m, 2H), 3.57 (s, 2H), 3.68 (m, 2H), 4.13 (m, 1H), 7.21 (m, 4H).

Preparation Example 55

1-(4-fluorobenzyl)-3-acetylthio-azetidine

Yield: 30.7%;
$^1$H NMR (200 MHz, CDCl$_3$): 2.30 (s, 3H), 3.11 (m, 2H), 3.60 (s, 2H), 3.71 (m, 2H), 4.14 (m, 1H), 7.03 (m, 2H), 7.22 (m, 2H).

Preparation Example 56

1-(3-trifluoromethylbenzyl)-3-acetylthio-azetidine

Yield: 20%;
$^1$H NMR (200 MHz, CDCl$_3$): 2.30 (s, 3H), 3.11 (m, 2H), 3.67 (s, 2H), 3.72 (m, 2H), 4.18 (m, 1H), 7.49 (m, 4H).

Preparation Example 57

1-[(1R)-1-phenylethyl]-3-acetylthio-azetidine

Yield: 20%;
$^1$H NMR (200 MHz, CDCl$_3$): 1.21 (d, J=6.5 Hz, 3H), 2.28 (s, 3H), 2.99 (t, J=7.3 Hz, 2H), 3.29 (q, J=6.5 Hz, 1H), 3.52 (t, J=7.3 Hz, 1H), 3.72 (t, J=7.3 Hz, 1H), 4.09 (qint, J=6.5 Hz, 1H), 7.25 (m, 5H).

Preparation Example 58

1-[(1S)-1-phenylethyl]-3-acetylthio-azetidine

Yield: 20%;
$^1$H NMR (200 MHz, CDCl$_3$): 1.20 (d, J=6.5 Hz, 3H), 2.28 (s, 3H), 2.99 (t, J=7.3 Hz, 2H), 3.29 (q, J=6.5 Hz, 1H), 3.52 (t, J=7.3 Hz, 1H), 3.72 (t, J=7.3 Hz, 1H), 4.09 (qint, J=6.9 Hz, 1H), 7.27 (m, 5H).

Preparation Example 59

1-(4-methylbenzyl)-3-acetylthio-azetidine

Yield: 54%;
$^1$H NMR (300 MHz, CDCl$_3$): δ 2.32 (s, 3H), 2.59 (s, 3H), 3.08 (m, 2H), 3.58 (s, 2H), 3.69 (m, 2H), 4.12 (m, 1H), 7.10 (d, 4H).

Preparation Example 60

1-[1-(4-bromophenyl)ethyl]-3-acetylthio-azetidine

Yield: 69%;
$^1$H NMR (300 MHz, CDCl$_3$): δ 1.18 (d, J=6.6 Hz, 3H), 2.28 (s, 3H), 2.98 (br, 2H), 3.26 (dd, J=6.6 Hz, J=12.9 Hz, 1H), 3.50 (t, 1H), 3.68 (t, 1H), 4.08 (m, J=5.7 Hz, 1H), 7.15 (d, J=13.2 Hz, 2H), 7.39 (d, J=13.2 Hz, 2H).

Preparation Examples 61 to 72

Preparation of 1-substituted benzyl-azetidine-3-thiol

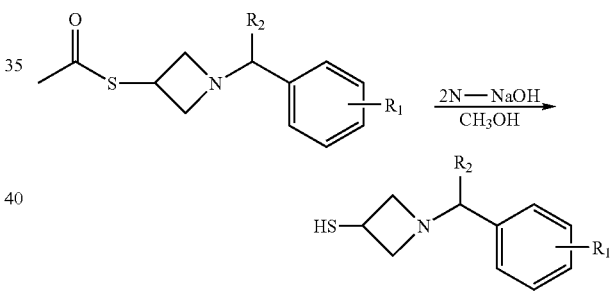

Preparation Example 61

1-benzyl-azetidine-3-thiol

1-Benzyl-3-acetylthio-azetidine (1 g, 4.518 mmol) prepared in Preparation Example 49 was dissolved in methanol (20 ml), and oxygen was completely removed by passing nitrogen through the mixture. The resulting mixture was cooled to 0° C., 2N sodium hydroxide (2.27 ml, 4.518 mmol) was added thereto slowly, stirred at 0° C. for 30 min, and then 2N—HCl was added thereto to neutralize (pH 7) the mixture. The resulting solution was concentrated under a reduced pressure, and the concentrate was dissolved in ethyl acetate, and washed with a saturated salt solution. The organic layer was dried over magnesium sulfate and concentrated under a reduced pressure to obtain 620 mg (yield: 77%) of the title compound, which was used in the next reaction without any additional purification.

The procedure of Preparation Example 61 was repeated employing each of the compounds of Preparation Examples 50 to 60 as a starting material to obtain the compounds of Preparation Examples 62 to 72, respectively.

Preparation Example 62

1-(4-methoxybenzyl)-azetidine-3-thiol

Yield: 93%.

Preparation Example 63

1-(3-methoxybenzyl)-azetidine-3-thiol

Yield: 100%.

Preparation Example 64

1-(2-methoxybenzyl)-azetidine-3-thiol

Yield: 83%.

Preparation Example 65

1-(3,4-dimethoxybenzyl)-azetidine-3-thiol

Yield: 100%.

Preparation Example 66

1-(4-chlorobenzyl)-azetidine-3-thiol

Yield: 80%.

Preparation Example 67

1-(4-fluorobenzyl)-azetidine-3-thiol

Yield: 98%.

Preparation Example 68

1-(3-trifluoromethylbenzyl)-azetidine-3-thiol

Yield: 90%.

Preparation Example 69

1-[(1R)-1-phenylethyl]-azetidine-3-thiol

Yield: 99%.

Preparation Example 70

1-[(1S)-1-phenylethyl]-azetidine-3-thiol

Yield: 67%.

Preparation Example 71

1-(4-methylbenzyl)-azetidine-3-thiol

Yield: 80%.

Preparation Example 72

1-[1-(4-bromophenyl)ethyl]-azetidine-3-thiol

Yield: 88%.

Examples 1 to 12

4-nitrobenzyl(1R,5S,6S)-2-(1-substituted benzyl-azetidine-3-yl-thio)-6-[(1R)-1-hydroxylethyl]-1-methylcarbapen-2-em-3-ester carboxylate

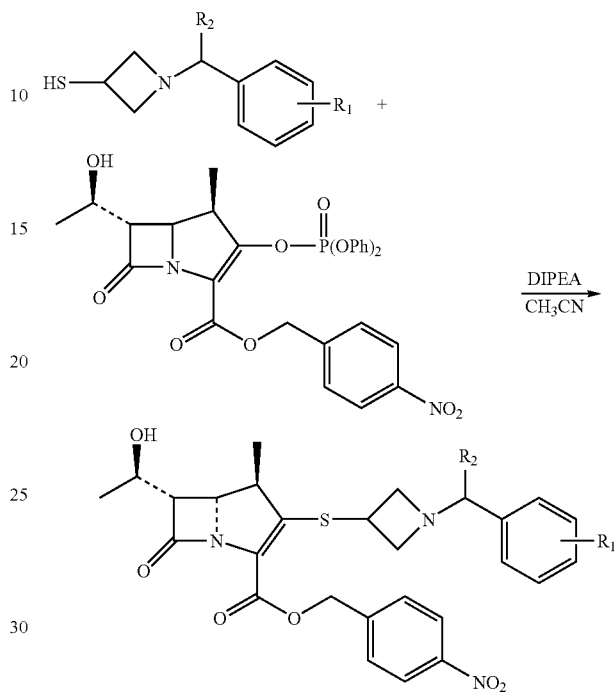

Example 1

4-nitrobenzyl(1R,5S,6S)-2-(1-benzyl-azetidine-3-yl-thio)-6-[(1R)-1-hydroxylethyl]-1-methylcarbapen-2-em-3-ester carboxylate 1-benzyl-azetidine-3-thiol (620 mg, 3.46 mmol) prepared in Preparation Example 61 was dissolved in acetonitrile (20 ml), and the mixture was cooled to a temperature raging from −20 to −10° C. Added to the mixture were diisopropylethylamine (733 μl, 4.21 mmol) and 4-nitrobenzyl(1R,5S,6S)-2-(diphenylphosphoryloxy)-6-[(1R)-1-hydroxyethyl]-1-methylcarbapen-2-em-3-ester carboxylate (2.09 g, 3.51 mmol) under a nitrogen atmosphere, and the resulting mixture was stirred at a temperature ranging from −20 to −10° C. for 2 hours. The resulting solution was extracted with ethyl acetate, the extract was washed with water then with a saturated salt solution, dried over anhydrous magnesium sulfate and concentrated under a reduced pressure. The concentrate was subjected to column chromatography (eluent–ethyl acetate/methanol=10/1) to obtain 720 mg (yield: 40%) of the title compound.

$^1$H NMR (200 MHz, CDCl$_3$) δ 1.21 (d, J=7.3 Hz, 3H), 1.36 (d, J=6.1 Hz, 3H), 3.12 (m, 2H), 3.22 (m, 2H), 3.63 (s, 2H), 3.77 (m, 2H), 3.97 (m, 1H), 4.20 (m, 2H), 5.36 (q, J=13.8 Hz, 53.3 Hz, 2H), 7.28 (m, 5H), 7.67 (d, J=8.9 Hz, 2H), 8.23 (d, J=8.9 Hz, 2H).

The procedure of Example 1 was repeated to obtain the compounds of Examples 2 to 12 employing each of the compounds of Preparation Examples 62 to 72 as a starting material.

Example 2

4-nitrobenzyl(1R,5S,6S)-2-[1-(4-methoxybenzyl)-azetidine-3-yl-thio]-6-[(1R)-1-hydroxylethyl]-1-methylcarbapen-2-em-3-ester carboxylate Yield: 32%;
$^1$H NMR (200 MHz, CDCl$_3$): δ 1.20 (d, J=7.3 Hz, 3H), 1.34 (d, J=6.1 Hz, 3H), 3.10 (m, 2H), 3.24 (m, 2H), 3.55 (s, 2H), 3.69 (m, 2H), 3.78 (s, 3H), 3.92 (m, 1H), 4.19 (m, 2H), 5.36 (q, J=13.8 Hz, 53.3 Hz, 2H), 6.84 (d, J=8.5 Hz, 2H), 7.16 (d, J=8.5 Hz, 2H), 7.65 (d, J=8.7 Hz, 2H), 8.22 (d, J=8.7 Hz, 2H).

Example 3

4-nitrobenzyl(1R,5S,6S)-2-[1-(3-methoxybenzyl)-azetidine-3-yl-thio]-6-[(1R)-1-hydroxylethyl]-1-methylcarbapen-2-em-3-ester carboxylate Yield: 34%;
$^1$H NMR (200 MHz, CDCl$_3$): δ 1.20 (d, J=6.9 Hz, 3H), 1.37 (d, J=6.1 Hz, 3H), 3.14 (m, 2H), 3.22 (m, 2H), 3.60 (s, 2H), 3.75 (m, 2H), 3.80 (s, 3H), 3.97 (m, 1H), 4.21 (m, 2H), 5.38 (q, J=13.8 Hz, 52.9 Hz, 2H), 6.80 (m, 3H), 7.21 (m, 1H), 7.67 (d, J=8.5 Hz, 2H), 8.24 (d, J=8.5 Hz, 2H).

Example 4

4-nitrobenzyl(1R,5S,6S)-2-[1-(2-methoxybenzyl)-azetidine-3-yl-thio]-6-[(1R)-1-hydroxylethyl]-1-methylcarbapen-2-em-3-ester carboxylate Yield: 42%;
$^1$H NMR (200 MHz, CDCl$_3$): δ 1.21 (d, J=7.3 Hz, 3H), 1.36 (d, J=6.1 Hz, 3H), 3.21 (m, 4H), 3.65 (s, 2H), 3.81 (m, 6H), 4.01 (m, 1H), 6.88 (m, 2H), 7.21 (m, 2H), 7.67 (d, J=8.3 Hz, 2H), 8.23 (d, J=8.1 Hz, 2H).

Example 5

4-nitrobenzyl(1R,5S,6S)-2-[1-(3,4-dimethoxybenzyl)-azetidine-3-yl-thio]-6-[(1R)-1-hydroxylethyl]-1-methylcarbapen-2-em-3-ester carboxylate Yield: 27%;
$^1$H NMR (200 MHz, CDCl$_3$): δ 1.21 (d, J=7.3 Hz, 3H), 1.35 (d, J=6.3 Hz, 3H), 3.08 (m, 2H), 3.22 (m, 2H), 3.56 (s, 2H), 3.74 (m, 2H), 3.85 (s, 3H), 3.87 (s, 3H), 3.99 (m, 1H), 4.20 (m, 2H), 5.38 (q, J=13.8 Hz, 53.5 Hz, 2H), 6.78 (s, 3H), 7.66 (d, J=9.0 Hz, 2H), 8.22 (d, J=8.8 Hz, 2H).

Example 6

4-nitrobenzyl(1R,5S,6S)-2-[1-(4-chlorobenzyl)-azetidine-3-yl-thio]-6-[(1R)-1-hydroxylethyl]-1-methylcarbapen-2-em-3-ester carboxylate Yield: 12%;
$^1$H NMR (200 MHz, CDCl$_3$): δ 1.22 (d, J=7.5 Hz, 3H), 1.36 (d, J=6.3 Hz, 3H), 3.11 (m, 2H), 3.25 (m, 2H), 3.58 (s, 2H), 3.72 (m, 2H), 3.95 (m, 1H), 4.20 (m, 2H), 5.35 (q, J=13.6 Hz, 54.1 Hz, 2H), 7.21 (m, 4H), 7.64 (m, 2H), 8.21 (d, J=8.7 Hz, 2H).

Example 7

4-nitrobenzyl(1R,5S,6S)-2-[1-(4-fluorobenzyl)-azetidine-3-yl-thio]-6-[(1R)-1-hydroxylethyl]-1-methylcarbapen-2-em-3-ester carboxylate Yield: 56%;
$^1$H NMR (200 MHz, CDCl$_3$): δ 1.19 (d, J=7.1 Hz, 3H), 1.34 (d, J=6.1 Hz, 3H), 3.07 (m, 2H), 3.21 (m, 2H), 3.57 (s, 2H), 3.73 (m, 2H), 3.95 (m, 1H), 4.21 (m, 2H), 5.38 (q, J=13.8 Hz, 53.7 Hz, 2H), 6.98 (m, 2H), 7.19 (m, 2H), 7.65 (d, J=9.0 Hz, 2H), 8.22 (d, J=9.0 Hz, 2H).

Example 8

4-nitrobenzyl(1R,5S,6S)-2-[1-(3-trifluoromethylbenzyl)-azetidine-3-yl-thio]-6-[(1R)-1-hydroxylethyl]-1-methylcarbapen-2-em-3-ester carboxylate Yield: 36%;
$^1$H NMR (200 MHz, CDCl$_3$): δ 1.23 (d, J=7.3 Hz, 3H), 1.37 (d, J=6.5 Hz, 3H), 3.17 (m, 2H), 3.22 (m, 2H), 3.68 (s, 2H), 3.74 (m, 2H), 4.00 (m, 1H), 4.21 (m, 2H), 5.49 (q, J=13.8 Hz, 53.7 Hz, 2H), 7.51 (m, 4H), 7.67 (d, J=8.9 Hz, 2H), 8.25 (d, J=9.0 Hz, 2H).

Example 9

4-nitrobenzyl(1R,5S,6S)-2-{1-[(1S)-1-phenylethyl]-azetidine-3-yl-thio}-6-[(1R)-1-hydroxylethyl]-1-methylcarbapen-2-em-3-ester carboxylate Yield: 36%;
$^1$H NMR (200 MHz, CDCl$_3$): δ 1.20 (d, J=7.3 Hz, 3H), 1.22 (J=6.1 Hz, 3H), 1.35 (d, J=6.5 Hz, 3H), 2.96 (t, J=7.1 Hz, 1H), 3.09 (t, 6.7 Hz, 1H), 3.22 (m, 2H), 3.31 (m, 1H), 3.47 (m, 1H), 3.88 (m, 2H), 4.09 (m, 3H), 5.38 (q, J=13.8 Hz, 54.3 Hz, 2H), 7.25 (m, 5H), 7.66 (d, J=9.0 Hz, 2H), 8.23 (d, J=9.0 Hz, 2H).

Example 10

4-nitrobenzyl(1R,5S,6S)-2-{1-[(1S)-1-phenylethyl]-azetidine-3-yl-thio}-6-[(1R)-1-hydroxylethyl]-1-methylcarbapen-2-em-3-ester carboxylate Yield: 25%;
$^1$H NMR (200 MHz, CDCl$_3$): δ 1.20 (d, J=7.3 Hz, 3H), 1.22 (J=6.2 Hz, 3H), 1.35 (d, J=6.5 Hz, 3H), 3.01 (m, 2H), 3.31 (m, 3H), 3.50 (m, 1H), 3.82 (m, 2H), 4.21 (m, 2H), 4.21 (m, 3H), 5.38 (q, J=13.8 Hz, 78.0 Hz, 2H), 7.67 (d, J=8.7 Hz, 2H), 8.23 (d, J=8.7 Hz, 2H).

Example 11

4-nitrobenzyl(1R,5S,6S)-2-[1-(4-methylbenzyl)-azetidine-3-yl-thio]-6-[(1R)-1-hydroxylethyl]-1-methylcarbapen-2-em-3-ester carboxylate Yield: 35%;
$^1$H NMR (200 MHz, CDCl$_3$): δ 1.21 (d, J=7.3 Hz, 3H), 1.35 (d, J=6.5 Hz, 3H), 2.32 (s, 3H), 3.11 (q, J=7.3 Hz, 2H), 3.22 (m, 2H), 3.58 (s, 2H), 3.78 (m, 2H), 3.98 (m, 1H), 4.18 (m, 2H), 5.39 (q, J=13.8 Hz, 52.9 Hz, 2H), 7.12 (s, 4H), 7.66 (d, J=8.5 Hz, 2H), 8.23 (d, J=9.0 Hz, 2H).

Example 12

4-nitrobenzyl(1R,5S,6S)-2-{1-[1-(4-bromophenyl)ethyl]-azetidine-3-yl-thio}-6-[(1R)-1-hydroxylethyl]-1-methylcarbapen-2-em-3-ester carboxylate Yield: 43%;
$^1$H NMR (200 MHz, CDCl$_3$): δ 1.21 (m, 6H), 1.36 (d, J=6.5 Hz, 3H), 2.98 (m, 3H), 3.11 (q, J=7.3 Hz, 2H), 3.22 (m, 2H), 3.58 (s, 2H), 3.78 (m, 2H), 3.98 (m, 1H), 3.05 (m, 1H), 3.23 (m, 3H), 3.44 (m, 1H), 3.81 (m, 2H), 4.20 (m, 2H), 5.37 (q, J=13.4 HZ, 53.3 Hz, 2H), 7.16 (d, J=8.1 Hz, 2H), 7.44 (d, J=8.5 Hz, 2H), 7.66 (d, J=9.0 Hz, 2H), 8.23 (d, J=8.5 Hz, 2H).

Examples 13 to 24

Potassium(1R,5S,6S)-2-(1-substituted benzyl-azetidine-3-yl-thio)-6-[(1R)-1-hydroxylethyl]-1-methylcarbapen-2-em-3-carboxylate

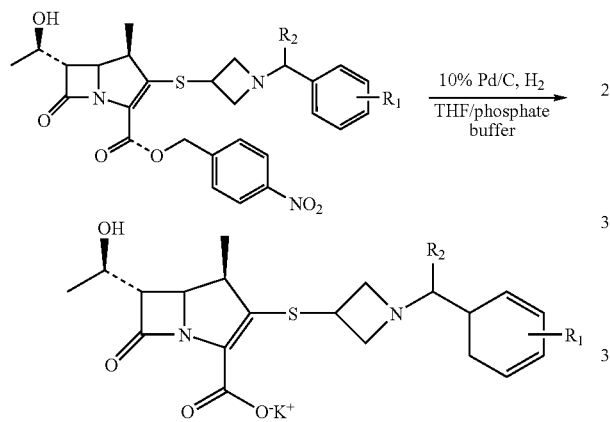

Example 13

Potassium(1R,5S,6S)-2-(1-benzyl-azetidine-3-yl-thio)-6-[(1R)-1-hydroxylethyl]-1-methylcarbapen-2-em-3-carboxylate 4-Nitrobenzyl(1R,5S,6S)-2-(1-benzyl-azetidine-3-yl-thio)-6-[(1R)-1-hydroxyethyl]-1-methylcarbapen-2-em-3-ester carboxylate (70 mg, 0.133 mmol) prepared in Example 1 was dissolved in THF (2 ml) and added thereto were potassium phosphate buffer (pH 7, 2 ml) and 10% palladium/carbon (20 mg) as a catalyst. The mixture was stirred under a hydrogen atmosphere (employing hydrogen balloon) at room temperature for 3 hours. The catalyst was removed by filtration, and the filtrate was concentrated under a reduced pressure. A small amount of water was added to the residue, and washed with ethyl carboxylate to remove impurities. The aqueous layer was subjected to C18 reverse phase column MPLC (eluent-water and 10% acetonitrile aqueous solution), and the product was collected and lyophilized to obtain 14 mg (yield: 27%) of the title compound.

$^1$H NMR (300 MHz, D$_2$O): δ 0.98 (d, J=6.9 Hz, 3H), 1.12 (d, J=6.1 Hz, 3H), 3.01 (m, 1H), 3.22 (m, 1H), 3.73 (m, 2H), 4.02 (m, 3H), 4.10 (s, 2H), 4.17 (m, 2H), 7.16 (m, 5H).

The procedure of Example 13 was repeated to obtain the compounds of Examples 14 to 24 employing each of the compounds prepared in Examples 2 to 12 as a starting material.

Example 14

Potassium(1R,5S,6S)-2-[1-(4-methoxybenzyl)-azetidine-3-yl-thio]-6-[(1R)-1-hydroxylethyl]-1-methylcarbapen-2-em-3-carboxylate Yield: 24%;
$^1$H NMR (300 MHz, D$_2$O): δ 1.07 (d, J=7.2 Hz, 3H), 1.21 (d, J=6.3 Hz, 3H), 3.08 (m, 1H), 3.35 (m, 1H), 3.77 (s, 2H), 3.86 (m, 3H), 4.07 (m, 2H), 4.18 (s, 3H), 4.33 (m, 2H), 7.33 (d, J=8.6 Hz, 2H).

Example 15

Potassium(1R,5S,6S)-2-[1-(3-methoxybenzyl)-azetidine-3-yl-thio]-6-[(1R)-1-hydroxylethyl]-1-methylcarbapen-2-em-3-carboxylate Yield: 15%;
$^1$H NMR (300 MHz, D$_2$O): δ 0.99 (d, J=6.9 Hz, 3H), 1.13 (d, J=6.5 Hz, 3H), 3.00 (m, 1H), 3.23 (m, 1H), 3.69 (s, 3H), 3.81 (m, 2H), 4.08 (m, 3H), 4.16 (s, 2H), 4.29 (m, 2H), 6.89 (m, 3H), 7.26 (m, 1H).

Example 16

Potassium(1R,5S,6S)-2-[1-(2-methoxybenzyl)-azetidine-3-yl-thio]-6-[(1R)-1-hydroxylethyl]-1-methylcarbapen-2-em-3-carboxylate Yield: 32%;
$^1$H NMR (300 MHz, D$_2$O): δ 0.84 (d, J=7.1 Hz, 3H), 0.99 (d, J=6.3 Hz, 3H), 2.90 (m, 1H), 3.10 (m, 1H), 3.19 (m, 2H), 3.56 (s, 3H), 3.62 (s, 2H), 3.72 (m, 3H), 3.86 (d, J=7.4 Hz, 1H), 3.92 (t, J=6.2 Hz, 1H), 6.76 (m, 2H), 7.00 (d, J=7.4 Hz, 1H), 7.11 (t, J=8.3 Hz, 1H).

Example 17

Potassium(1R,5S,6S)-2-[1-(3,4-dimethoxybenzyl)-azetidine-3-yl-thio]-6-[(1R)-1-hydroxylethyl]-1-methylcarbapen-2-em-3-carboxylate Yield: 24%;
$^1$H NMR (300 MHz, D$_2$O): δ 0.99 (d, J=7.3 Hz, 3H), 1.13 (d, J=6.1 Hz, 3H), 3.63 (m, 2H), 3.71 (s, 6H), 3.98 (s, 2H), 4.04 (m, 5H), 6.87 (bs, 3H).

Example 18

Potassium(1R,5S,6S)-2-[1-(4-chlorobenzyl)-azetidine-3-yl-thio]-6-[(1R)-1-hydroxylethyl]-1-methylcarbapen-2-em-3-carboxylate Yield: 11%;
$^1$H NMR (300 MHz, D$_2$O): δ 0.99 (d, J=6.9 Hz, 3H), 1.15 (d, J=6.5 Hz, 3H), 3.08 (m, 3H), 3.21 (m, 1H), 3.53 (s, 2H), 3.58 (m, 2H), 3.80 (m, 1H), 4.01 (m, 1H), 7.14 (d, J=8.1 Hz, 2H), 7.27 (d, J=8.1 Hz, 2H).

Example 19

Potassium(1R,5S,6S)-2-[1-(4-fluorobenzyl)-azetidine-3-yl-thio]-6-[(1R)-1-hydroxylethyl]-1-methylcarbapen-2-em-3-carboxylate Yield: 36%;
$^1$H NMR (300 MHz, D$_2$O): δ 1.17 (d, J=7.3 Hz, 3H), 1.31 (d, J=6.1 Hz, 3H), 3.20 (m, 1H), 3.41 (m, 1H), 3.69 (m, 2H), 4.07 (s, 2H), 4.18 (m, 5H), 7.20 (m, 2H), 7.40 (m, 2H).

Example 20

Potassium(1R,5S,6S)-2-[1-(3-trifluoromethylbenzyl)-azetidine-3-yl-thio]-6-[(1R)-1-hydroxylethyl]-1-methylcarbapen-2-em-3-carboxylate Yield: 58%;

$^1$H NMR (300 MHz, D$_2$O): δ 0.99 (d, J=6.9 Hz, 3H), 1.14 (d, J=6.5 Hz, 3H), 3.16 (m, 2H), 3.21 (m, 2H), 3.65 (m, 4H), 3.82 (m, 1H), 4.00 (m, 1H), 4.08 (m, 1H), 7.40 (m, 2H), 7.53 (m, 2H).

Example 21

Potassium(1R,5S,6S)-2-{1-[(1R)-1-phenylethyl]-azetidine-3-yl-thio}-6-[(1R)-1-hydroxylethyl]-1-methylcarbapen-2-em-3-carboxylate Yield: 58%;

$^1$H NMR (300 MHz, D$_2$O): δ 0.83 (d, J=7.2 Hz, 3H), 0.98 (d, J=6.3 Hz, 3H), 1.12 (d, J=6.5 Hz, 3H), 2.87 (t, J=7.4 Hz, 1H), 3.11 (m, 1H), 3.32 (m, 2H), 3.85 (m, 6H), 7.15 (m, 5H).

Example 22

Potassium(1R,5S,6S)-2-{1-[(1S)-1-phenylethyl]-azetidine-3-yl-thio}-6-[(R)-1-hydroxylethyl]-1-methylcarbapen-2-em-3-carboxylate Yield: 49%;

$^1$H NMR (300 MHz, D$_2$O): δ 0.83 (d, J=7.2 Hz, 3H), 0.98 (d, J=6.3 Hz, 3H), 1.12 (d, J=6.5 Hz, 3H), 2.87 (t, J=7.4 Hz, 1H), 3.11 (m, 1H), 3.32 (m, 2H), 3.85 (m, 6H), 7.15 (m, 5H).

Example 23

Potassium(1R,5S,6S)-2-[1-(4-methylbenzyl)-azetidine-3-yl-thio]-6-[(1R)-1-hydroxylethyl]-1-methylcarbapen-2-em-3-carboxylate Yield: 29%;

$^1$H NMR (300 MHz, D$_2$O): δ 0.99 (d, J=6.9 Hz, 3H), 1.13 (d, J=6.1 Hz, 3H), 2.18 (s, 3H), 3.04 (t, J=7.2 Hz, 1H), 3.23 (m, 1H), 3.61 (m, 2H), 4.01 (m, 7H), 7.13 (m, 4H).

Example 24

Potassium(1R,5S,6S)-2-{1-[1-(4-bromophenyl)ethyl]-azetidine-3-yl-thio}-6-[(1R)-1-hydroxylethyl]-1-methylcarbapen-2-em-3-carboxylate Yield: 43%;

$^1$H NMR (300 MHz, D$_2$O): δ 0.84 (d, J=7.2 Hz, 3H), 1.16 (d, J=6.3 Hz, 3H), 1.18 (d, J=6.5 Hz, 3H), 2.98 (m, 2H), 3.17 (m, 1H), 3.43 (m, 2H), 3.72 (m, 2H), 3.91 (m, 2H), 4.08 (m, 1H), 7.04 (d, J=8.1 Hz, 2H), 7.28 (d, J=8.1 Hz, 2H).

Test Example 1

Measurement of Minimum Inhibitory Concentration (MIC)

The antibacterial activities of the compounds of the present invention prepared in the above Examples against Gram-positive and Gram-negative bacteria, MRSA and QRS were tested as follows.

Respective bacterial strains were inoculated into 3 ml of Fleisch extract broth (beef extract 1%, peptone 1%, NaCl 0.3%, Na$_2$HPO$_4$.12H$_2$O 0.2%, pH 7.4-7.5. 10% horse serum was supplemented for *Streptococcus pyogenes* and *S. facium*) and cultured on a shaking incubator at 37° C. for 18 hours. About 10$^4$ CFU/spot of the cultured bacterial strains were inoculated onto Müller-Hinton agar plates containing serial double dilutions (final concentration of 0.002 to 100 μg/ml) of a test compound employing an automatic inoculator (Dynatech, USA), and incubated at 37° C. for 18 hours. When the incubation was completed, the minimum inhibitory concentration was determined. The results are shown in Table 1 and Table 2. Meropenem (Yuhan corporation, Korea) and vancomycin (Cj Inco., Korea) were used as standard antibiotics, respectively.

TABLE 1

| strains | MIC (μg/ml) | | | | | | | |
|---|---|---|---|---|---|---|---|---|
| | Exam. 13 | Exam. 14 | Exam. 16 | Exam. 17 | Exam. 19 | Exam. 22 | meropenem | vancomycin |
| *Staphylococcus pyogenes* 308A | 0.002 | 0.002 | 0.002 | 0.002 | 0.002 | 0.002 | 0.007 | 0.781 |
| *Staphylococcus pyogenes* 77A | 0.002 | 0.002 | 0.002 | 0.002 | 0.002 | 0.002 | 0.004 | 0.391 |
| *Staphylococcus faecium* MD 8b | 1.563 | 1.563 | 1.563 | 1.563 | 1.563 | 1.563 | 6.250 | 0.391 |
| *Staphylococcus aureus* 285 | 0.025 | 0.098 | 0.025 | 0.025 | 0.025 | 0.025 | 0.098 | 0.391 |
| *Staphylococcus aureus* 503 | 0.013 | 0.025 | 0.013 | 0.013 | 0.013 | 0.013 | 0.049 | 0.391 |
| *Escherichia coli* 078 | 0.049 | 0.013 | 0.098 | 0.098 | 0.025 | 0.098 | 0.025 | 100.00 |
| *Escherichia coli* DC 0 | 0.098 | 0.049 | 0.781 | 0.781 | 0.098 | 0.391 | 0.025 | 100.00 |
| *Escherichia coli* DC 2 | 0.025 | 0.049 | 0.049 | 0.049 | 0.025 | 0.025 | 0.025 | 50.000 |
| *Escherichia coli* TEM | 0.049 | 0.195 | 0.195 | 0.391 | 0.049 | 0.391 | 0.025 | 100.00 |

TABLE 1-continued

| | MIC (μg/ml) | | | | | | | |
|---|---|---|---|---|---|---|---|---|
| strains | Exam. 13 | Exam. 14 | Exam. 16 | Exam. 17 | Exam. 19 | Exam. 22 | meropenem | vancomycin |
| Escherichia coli 1507 E | 0.049 | 0.098 | 0.195 | 0.391 | 0.049 | 0.195 | 0.025 | 100.00 |
| Salmonella typhimurium 179 | 0.049 | 0.098 | 0.098 | 0.098 | 0.049 | 0.049 | 0.049 | 100.00 |
| Klebsiella oxytoca 1082 E | 0.049 | 0.098 | 0.098 | 0.098 | 0.049 | 0.098 | 0.049 | 100.00 |
| Klebsiella aerogenes 1522 E | 0.098 | 0.195 | 0.391 | 0.391 | 0.098 | 0.391 | 0.049 | 100.00 |
| Enterobacter cloacae P 99 | 0.098 | 0.391 | 0.391 | 0.781 | 0.098 | 0.391 | 0.049 | 100.00 |
| Enterobacter cloacae 1321 E | 0.049 | 0.098 | 0.098 | 0.391 | 0.049 | 0.098 | 0.025 | 100.00 |

TABLE 2

| | | MIC (μg/ml) | | | | | | | |
|---|---|---|---|---|---|---|---|---|---|
| | strain | Exam. 13 | Exam. 14 | Exam. 16 | Exam. 17 | Exam. 19 | Exam. 22 | Meropenem | Vancomycin |
| MRSA | Staphylococcus aureus 88E | 0.025 | 0.1951 | 0.025 | 0.195 | 0.049 | 0.025 | 0.195 | 0.781 |
| | Staphylococcus aureus 121E | 0.025 | 0.098 | 0.025 | 0.098 | 0.049 | 0.049 | 0.195 | 0.781 |
| | Staphylococcus aureus 208E | 0.049 | 0.049 | 0.025 | 0.049 | 0.025 | 0.025 | 0.098 | 0.781 |
| | Staphylococcus aureus 256E | 0.013 | 0.025 | 0.025 | 0.049 | 0.025 | 0.025 | 0.049 | 0.781 |
| | Staphylococcus aureus 690E | 0.391 | 0.391 | 0.195 | 0.781 | 0.391 | 0.195 | 3.125 | 0.391 |
| | Staphylococcus aureus 692E | 0.025 | 0.391 | 0.049 | 0.195 | 0.025 | 0.025 | 0.098 | 0.781 |
| | Staphylococcus aureus 693E | 3.125 | 0.391 | 1.563 | 0.391 | 3.125 | 3.125 | 6.250 | 1.563 |
| | Staphylococcus aureus 694E | 1.563 | 0.098 | 0.049 | 0.098 | 3.125 | 0.049 | 6.250 | 1.563 |
| | Staphylococcus aureus 695E | 0.391 | 0.098 | 0.049 | 0.098 | 0.195 | 0.098 | 0.781 | 1.563 |
| | Staphylococcus aureus 697E | 0.025 | 0.195 | 0.025 | 0.098 | 0.049 | 0.025 | 0.098 | 0.781 |
| QRS | Staphylococcus aureus 179 | 0.049 | 0.049 | 0.049 | 0.098 | 0.049 | 0.049 | 0.195 | 0.781 |
| | Staphylococcus aureus 241 | 0.049 | 0.049 | 0.025 | 0.195 | 0.049 | 0.049 | 0.195 | 0.781 |
| | Staphylococcus aureus 293 | 0.098 | 0.098 | 0.098 | 0.391 | 0.195 | 0.195 | 0.781 | 0.781 |
| | Staphylococcus epidermidis 178 | 0.391 | 0.391 | 0.195 | 0.781 | 0.195 | 0.195 | 0.781 | 1.563 |
| | Staphylococcus epidermidis 291 | 0.391 | 0.391 | 0.391 | 1.563 | 0.391 | 0.391 | 1.563 | 1.563 |

As can be seen in Tables 1 and 2, the carbapenem derivatives of the present invention exhibited superior antibacterial activities against standard strains of Gram-positive and Gram-negative bacteria and also against MRSA and QRS as resistant strains over the standard antibiotics (meropenem and vancomycin).

Test Example 2

Test of Pharmacokinetics in Animals

The pharmacokinetics of the carbapenem derivatives of the present invention was determined using mice. Each of the compounds of Examples 13 and 14 and meropenem (a positive control) was dissolved in distilled water, and mice were orally administered (PO) or subcutaneously injected (SC) at a dosage of 40 mg/kg body weight (I.C.R mice, weighing 22 to 25 g, 4 mice/group). Blood samples were withdrawn from mice tails using heparinated capillaries at 10 min., 20 min., 30 min., 45 min., 1 hour, 2 hours, 3 hours and 4 hours after the administration.

Standard antibiotic samples were prepared by serial two-fold dilution with control blood. Agar plates were prepared with Müller-Hinton agar medium containing 6.7% sheep blood and 1% *Streptococcus pyogenes* 77A culture solution, and the diluted standard and blood samples were added to wells formed on the plates. The plate was stored at 4° C. for 1 hour to allow the sample to spread, and incubated at 37° C. for 18 hours. PK (pharmacokinetic) change indicators (AUC, $T_{max}$, $C_{max}$ and $T_{1/2}$) of the test compound concentration remaining in the mouse blood over time were assayed over a set period. The result is shown in Table 3.

TABLE 3

| medicament | Administration | AUC*1 (μg·h/ml) | $T_{max}$*2 (hr) | $C_{max}$*3 (μg/ml) | $T_{1/2}$*4 (hr) |
|---|---|---|---|---|---|
| Exam. 13 | SC | 94.76 | 0.22 | 86.83 | 0.92 |
|  | PO | 1.73 | 0.49 | 1.06 | 0.81 |
| Exam. 14 | SC | 79.66 | 0.25 | 69.61 | 0.76 |
|  | PO | 5.20 | 0.44 | 2.07 | 2.06 |
| Meropenem | SC | 7.50 | 0.33 | 13.39 | 0.43 |
|  | PO | N.D | N.D | N.D | N.D |

*1 area under blood-medicament concentration curve till 24 hours from administration
*2 time at the point of maximum blood-medicament concentration
*3 maximum blood-medicament concentration
*4 half time of blood-medicament concentration
N.D: Not detected As can be seen in Table 3, the compounds of Example 13 and 14 showed 10 to 12 times higher AUC and a more than 2 times increase in $T_{1/2}$ than meropenem, and unlike meropenem, the compounds of Example 13 and 14 were absorbed through the oral route to significant extents. Thus, the compounds of the present invention exhibit excellent pharmacokinetics.

Then, pharmacokinetical assay (amount of medicament administered was 20 mg/kg) was carried out as above using rats.

TABLE 4

| medicament | Administration | AUC*1 (μg·h/ml) | $T_{max}$*2 (hr) | $C_{max}$*3 (μg/ml) | $T_{1/2}$*4 (hr) |
|---|---|---|---|---|---|
| Exam. 14 | SC | 34.58 | 0.37 | 35.85 | 0.69 |
|  | PO | 0.33 | 0.71 | 0.20 | 5.07 |
| Meropenem | SC | 2.05 | 0.25 | 3.92 | 0.31 |
|  | PO | N.D | N.D | N.D | N.D |

*1 area under blood-medicament concentration curve till 24 hours after administration
*2 time at the point of maximum blood-medicament concentration
*3 maximum blood-medicament concentration
*4 half time of blood-medicament concentration
N.D: not detected As can be seen in Table 4, in rats, the compound of Example 14 showed 17 times higher AUC and a more than 2 times increase in $T_{1/2}$ than meropenem, and unlike meropenem, the compound of Example 14 was absorbed through the oral route to a significant extent. Thus, the compound of the present invention exerted equally good pharmacokinetic profiles in rats.

Test Example 3

Determination of Protection Dose ($PD_{50}$) in Infected Animal Model

In order to get the lethal dose ($LD_{100}$) of bacteria, *Staphylococcus pyogenes* 77A and *Escherichia coli* 078 were each diluted by $10^2 \sim 10^9$ times. The CFU (colony forming unit) of each bacterial solution was calculated, and the diluted bacterial solution was intraperitoneally administered to mice and the death was observed for 7 days. For a main experiment, 3 to 4 week-old SPF ICR male mice were divided into 4 groups each of 8 to 10 mice, and fasted for 24 hours before a test. The solutions of *Staphylococcus pyogenes* 77A and *Escherichia coli* 078 were concentrated to a level that was 2 to 10 times of $LD_{100}$, and the concentrated *Staphylococcus pyogenes* 77A solution mixed with 10% horse serum and the concentrated *Escherichia coli* 078 solution mixed with 5% hog gastric mucin were each injected intraperitoneally into the mice of each group to induce whole body infection.

The serially diluted solutions of the compound of Example 14 or meropenem (5 different concentrations) were injected intraperitoneally into the infected mice 1 hour after the infection. All of the mice in the control group injected with physiological salt solution died within 48 hours. The number of survived mouse in each group injected with antibacterial material, were counted to determine $PD_{50}$, and the 95% confidence interval thereof was calculated employing Probit method. The result is shown in Table 5.

TABLE 5

|  | *Staphylococcus pyogenes* 77A | *Escherichia coli* 078 |
|---|---|---|
| Exam. 14 | 3.05 | 1.44 |
|  | (2.19-4.45) | (0.83-2.27) |
| Meropenem | 9.13 | 3.31 |
|  | (7.5-15.0) | (2.03-5.40) | unit: mg/kg
( ): 95% confidence interval

As can be seen in Table 5, the compound of Example 14 provided higher efficacy against *Staphylococcus pyogenes* or *Escherichia coli* than meropenem.

Test Example 4

Sensitivity Assay Against Dihydropeptidase-1 (DHP-1)

The rate of degradation of the inventive compounds by the action of DHP-1 enzyme extracted from hog kidney was determined as follow.

0.3 mg of the compounds of Example 13 to 24 (test materials), meropenem and imipenem (Choongwae pharma. Corp., control materials) were dissolved in 50 mM MOPS buffer to a concentration of 500 μg/ml. 0.2 unit of the enzyme was allowed to react with the above solution at 30° C., and the absorbance at 299 nm of the remaining medicament was measured to determine the degradation rate. The absorbance was measured at 0, 0.5, 1, 2 and 4 hour points, and $T_{1/2}$, the time when the concentration of the medicament become the half, was obtained by regression analysis. Relative $T_{1/2}$ was calculated based on $T_{1/2}$=1.0 for meropenem. The result is shown in Table 6.

TABLE 6

| medicament | $T_{1/2}$ | Relative $T_{1/2}$ |
|---|---|---|
| Exam. 13 | 19.28 | 1.10 |
| Exam. 14 | 19.88 | 1.13 |
| Exam. 15 | 28.16 | 1.54 |
| Exam. 16 | 200.91 | 9.81 |
| Exam. 17 | 27.45 | 1.54 |
| Exam. 18 | 15.36 | 0.84 |
| Exam. 19 | 28.16 | 1.54 |
| Exam. 20 | 16.03 | 0.88 |
| Exam. 21 | 38.43 | 1.88 |
| Exam. 22 | 65.99 | 3.22 |
| Exam. 23 | 25.24 | 1.38 |
| Exam. 24 | 19.71 | 1.08 |
| Meropenem | 18.29 | 1.00 |
| Imipenem | 2.39 | 0.13 |

As can be seen in Table 6, the compounds of the present invention were hydrolyzed more slowly than the standard materials, and especially the compounds of Example 16 and 22 were very stable. Thus, the compounds of the present invention are useful medicaments, which overcome the disadvantage, rapid degradation of carbapenem antibacterial agent by DHP-1 enzyme.

Test Example 5

Acute Toxicity Test

The acute toxicity of the compound of Example 14 was tested using several groups of ICR mice each of 10 mice. 500 mg/kg, 1,000 mg/kg and 2,000 mg/kg doses of the medicament were each intraperitoneally injected into each group of mice, and the temperature change, weight change and death were observed for 7 days after the injection. As a result, no mice died, and no distinct temperature change nor weight loss were observed. Thus, $LD_{50}$ was placed at a level higher than 2,000 mg/kg. The compound of Example 14 is thus a largely non-toxic antibiotic.

While the invention has been described with respect to the above specific embodiments, it should be recognized that various modifications and changes maybe made to the invention by those skilled in the art which also fall within the scope of the invention as defined by the appended claims.

What is claimed is:
1. A 2-arylmethylazetidine carbapenem derivative of formula (I) or a pharmaceutically acceptable salt thereof:

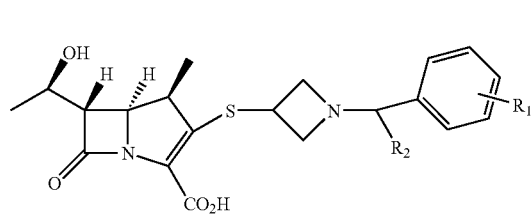

wherein,
R1 is hydrogen atom, or one or more substituents selected from the group consisting of $C_{1-3}$ alkyl, $C_{1-3}$ alkyloxy, trifluoromethyl and halogen atom; and
R2 is hydrogen atom or $C_{1-3}$ alkyl.
2. The compound of claim 1, which is selected from the group consisting of:
Potassium(1R,5S,6S)-2-(1-benzyl-azetidine-3-yl-thio)-6-[(1R)-1-hydroxyethyl]-1-methylcarbapen-2-em-3-carboxylate;
Potassium(1R,5S,6S)-2-[1-(4-methoxybenzyl)-azetidine-3-yl-thio]-6-[(1R)-1-hydroxyethyl]-1-methylcarbapen-2-em-3-carboxylate;
Potassium(1R,5S,6S)-2-(3-methoxybenzyl)-azetidine-3-yl-thio]-6-[(1R)-1-hydroxyethyl]-1-methylcarbapen-2-em-3-carboxylate;
Potassium(1R,5S,6S)-2-[1-(2-methoxybenzyl)-azetidine-3-yl-thio]-6-[(1R)-1-hydroxyethyl]-1-methylcarbapen-2-em-3-carboxylate;
Potassium(1R,5S,6S)-2-[1-(3,4-dimethoxybenzyl)-azetidine-3-yl-thio]-6-[(1R)-1-hydroxyethyl]-1-methylcarbapen-2-em-3-carboxylate;
Potassium(1R,5S,6S)-2-[1-(4chlorobenzyl)-azetidine-3-yl-thio]-6-[(1R)-1-hydroxyethyl]-1-methylcarbapen-2-em-3-carboxylate;
Potassium(1R,5S,6S)-2-[(1-(4-fluorobenzyl)-azetidine-3-yl-thio)-6-[(1R)-1-hydroxyethyl]-1-methylcarbapen-2-em-3-carboxylate;
Potassium(1R,5S,6S)-2-[1-(3-trifluoromethylbenzyl)-azetidine-3-yl-thio]-6-[(1R)-1-hydroxyethyl]-1-methylcarbapen-2-em-3-carboxylate;
Potassium(1R,5S,6S)-2-{1-[(1R)-1-phenylethyl]-azetidine-3-yl-thio}-6-[(1R)-1-hydroxyethyl]-1-methylcarbapen-2-em-3-carboxylate;
Potassium(1R,5S,6S)-2-{1-[(1S)-1-phenylethyl]-azetidine-3-yl-thio}-6-[(1R)-1-hydroxyethyl]-1-methylcarbapen-2-em-3-carboxylate;
Potassium(1R,5S,6S)-2-[1-(4-methylbenzyl)-azetidine-3-yl-thio]-6-[(1R)-1-hydroxyethyl]-1-methylcarbapen-2-em-3-carboxylate; and
Potassium(1R,5S,6S)-2-{1-[1-(4-bromophenyl)ethyl]-azetidine-3 yl-thio}-6-[(1R)-1-hydroxyethyl]-1-methylcarbapen-2-em-3-carboxylate.
3. A process for preparing a 2-arylmethylazetidine carbapenem derivative of formula (I) or a pharmaceutically acceptable salt thereof, which comprises the steps of:
subjecting compounds of formula (II) and formula (III) to a condensation reaction to obtain a carbapenem ester derivative of formula (1\0;
and
removing the carboxyl protecting group and the optional hydroxyl protecting group from the compound of formula (IV)

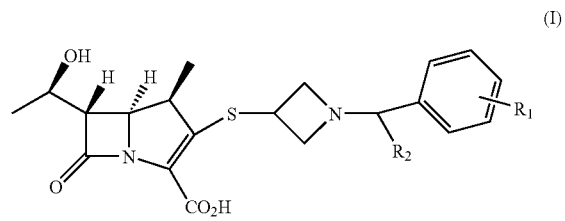

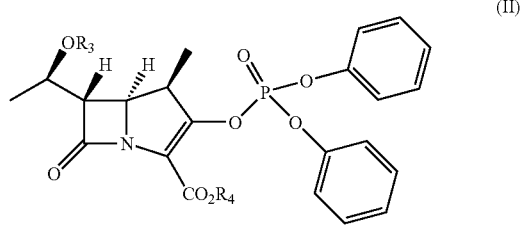

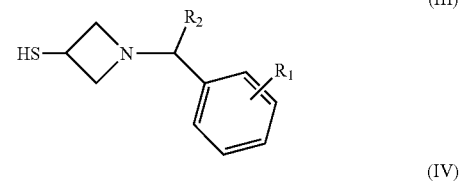

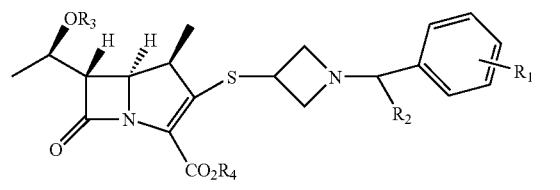

wherein,
$R_1$ is hydrogen atom, or one or more substituents selected from the group consisting of $C_{1-3}$ alkyl, $C_{1-3}$ alkyloxy, trifluoromethyl and halogen atom;
R2 is hydrogen atom or $C_{1-3}$ alkyl,
R3 is hydrogen atom or a hydroxyl protecting group; and
R4 is a carboxyl protecting group.

4. The process of claim 3, wherein step (a) is carried out by reacting the compounds of formula (II) and formula (111) in an organic solvent under the presence of diisopropylethylamine or triethylamine at a temperature ranging from −20 to 0° C. for 2 to 4 hours.

5. The process of claim 4, wherein the organic solvent is selected from the group consisting of acetonitrile, methylene chloride, tetrahydrofuran and acetone.

6. The process of claim 3, wherein the compound of formula (III) is prepared by a process comprising the steps of: (a) reacting a compound of formula (V) and epichlorohydrin in an organic solvent with stirring at room temperature for 24 to 48 hours to obtain a compound of formula (VI);
  (b) reacting the compound of formula (VI) and N-trimethylsilylacetamide in an organic solvent with heating for 3 to 5 hours to obtain a compound of formula (VII);
  (c) heat-refluxing the compound of formula (VII) for 3 to 5 days in an organic solvent under the presence of an organic salt to obtain a compound of formula (VI);
  (d) dissolving the compound of formula (VID in an alcohol, adding an alkali thereto, and stirring the mixture at room temperature for 30 mm to 1 hour to obtain a compound of formula (E);
  (e) subjecting the compound of formula (IX) to the Mitsunobu reaction to obtain a compound of formula (X); and
  (f) hydrolyzing the compound of formula (X) in an alcohol by adding an aqueous sodium hydroxide solution to obtain the compound of formula (III)

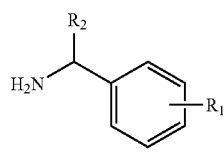

(V)

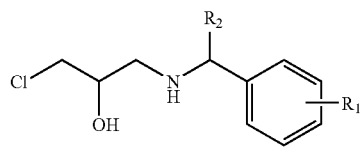

(VI)

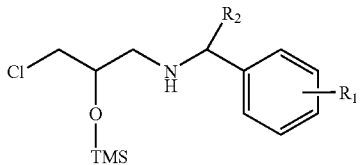

(VII)

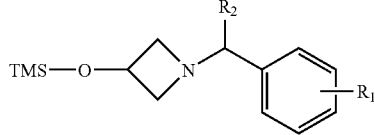

(VIII)

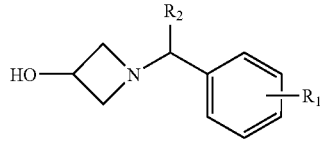

(IX)

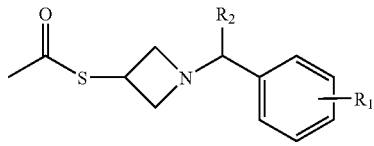

(X)

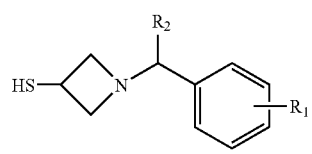

(III)

wherein,

R1 and R2 have the same meanings as defined in claim 3.

7. The process of claim 6, wherein the organic solvent used in steps (a) and (b) is petroleum ether, ethyl ether or ligroin.

8. The process of claim 6, wherein the organic solvent used in step (c) is acetonitrile, tetrahydrofuran or methylene chloride, and the organic base is triethylamine or diisopropylethylamine.

9. The process of claim 6, wherein the alcohol used in step (d) is methanol or ethanol, and the alkali is sodium methoxide, lithium hydroxide or potassium tert-butoxide.

10. An antibacterial composition comprising the carbapenem derivative of formula (I) according to claim 1 or a pharmaceutically acceptable salt thereof according to claim 1 as an active ingredient together with a pharmaceutically acceptable carrier.

* * * * *

UNITED STATES PATENT AND TRADEMARK OFFICE
CERTIFICATE OF CORRECTION

PATENT NO. : 7,662,810 B2 Page 1 of 1
APPLICATION NO. : 11/578007
DATED : February 16, 2010
INVENTOR(S) : Kim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 644 days.

Signed and Sealed this

Twenty-eighth Day of December, 2010

David J. Kappos
*Director of the United States Patent and Trademark Office*